United States Patent [19]

Potgeiter

[11] Patent Number: 6,066,787
[45] Date of Patent: May 23, 2000

[54] HYBRID SUNFLOWER PLANT AND SEED PAN 9501

[75] Inventor: Johan J. W. Potgeiter, Delmas, South Africa

[73] Assignee: Pannar Seed Limited, Dorset, United Kingdom

[21] Appl. No.: 09/216,779

[22] Filed: Dec. 18, 1998

Related U.S. Application Data

[60] Provisional application No. 60/069,995, Dec. 18, 1997.

[51] Int. Cl.$^7$ ............................... A01H 5/00; A01H 5/10; A01H 1/04; C12N 5/04
[52] U.S. Cl. .......................... 800/322; 800/260; 435/428; 435/416
[58] Field of Search ..................................... 800/298, 322, 800/260, 271, 272, 274; 435/428, 416

[56] References Cited

U.S. PATENT DOCUMENTS

| | | | |
|---|---|---|---|
| 4,552,844 | 11/1985 | Everett | 435/240 |
| 4,670,391 | 6/1987 | Cooley et al. | 435/240 |
| 4,670,392 | 6/1987 | Cooley et al. | 435/240 |
| 4,673,648 | 6/1987 | Wilcox et al. | 435/240 |
| 4,681,849 | 7/1987 | Paterson et al. | 435/240 |
| 4,687,743 | 8/1987 | Paterson et al. | 435/240.49 |
| 5,017,491 | 5/1991 | Freyssinet et al. | 435/240.5 |
| 5,030,572 | 7/1991 | Power et al. | 435/240.5 |

OTHER PUBLICATIONS

Catalogue Officiel Des Espéces Et Variétés (1997).
23 nouveaux hybrides de tournesol pour 1994 (previously reported as French Sunflower Registration Trials) (1995).
CTPS French Performance Trial Results (1995).
Promotional Brochure "Tournesol Labrador" (1995).
Cetium French Performance Trial Results (1996).
Murashige, T., et al., "A Revised Medium for Rapid Growth and Bioassays with Tobacco Tissue Cultures," Physiol. Plant., 15:473–497, (1962).
Fick, G.N., "Breeding and Genetics," IN Sunflower Science and Technology, 279–338, (1978).
Heiser, Jr., C.B., "Taxonomy of *Helianthus* and Origin of Domesticated Sunflower," IN Sunflower Science and Technology, 31–53, (1978).
Knowles, P.F., "Morphology and Anatomy," IN Sunflower Science and Technology, 55–87, (1978).
Espinasse, A., et al., "Shoot Regeneration of Callus Derived from Globular Torpedo Embryos from 59 Sunflower Genotypes," Crop Science, 29(1):201–205, (1989).
Bracken, G.K., "A Damage Index for Estimating Yield Loss in Sunflowers Caused by Sunflower Midge," Can. J. Plant Sci., 71:81–85, (1991).
Chraibi, K.M.B., et al., "A Genotype–Independent System of Regeneration from Cotyledons of Sunflower (*Helianthus annuus* L.). The Role of Ethylene," Plant Science, 86:215–221, (1992).
Chraibi, K.M.B., et al., "Enhancement of Shoot Regeneration Potential by Liquid Medium Culture from Mature Cotyledons of Sunflower (*Helianthus annuus* L.)," Plant Cell Reports, 10:617–620, (1992).
Alibert, G., et al., "Sunflower Tissue and Cell Cultures and Their Use in Biotechnology," Plant Physiol. Biochem., 32(1):31–44, (1994).
Bergland, D., "North Dakota Hybrid Sunflower Performance Testing 1998," NDSU Extension Service Publication, A–652 (Revised):1–32, (1999).
UPOV–ROM 1998/04 Sunflower Labrador, OE, ZZZ FR0000015805, 1999.
UPOV–ROM 1998/04 Sunflower Labrador, FR, NLI 138586, 1993.
UPOV–ROM 1998/04 Sunflower Labrador, ES, NLI 008001518, 1991.

*Primary Examiner*—Lynette R. F. Smith
*Assistant Examiner*—Melissa L. Kimball
*Attorney, Agent, or Firm*—Patterson & Keough, P.A.

[57] ABSTRACT

According to the invention there is provided a hybrid sunflower seed and plant, designated PAN 9501. Further provided are regenerable tissue, callus and sunflower plants regenerated from the regenerable tissue and callus. Also provided is a process of producing a hybrid sunflower seed designated PAN 9501 and a process of producing a sunflower seed from hybrid sunflower PAN 9501. Further yet provided is a sunflower zygote arising from a fertilization of a gamete, the gamete arising from hybrid sunflower PAN 9501, the gamete an egg cell or a sperm nucleus, a sunflower seed arising from the zygote, and a sunflower plant arising from the sunflower seed. Finally a sunflower plant and its parts produced by hybrid sunflower seed designated PAN 9501 are provided.

13 Claims, No Drawings

HYBRID SUNFLOWER PLANT AND SEED PAN 9501

CROSS-REFERENCES TO RELATED APPLICATIONS

This application claims priority under 35 U.S.C. § 119(e) to U.S. Provisional Application No. 60/069,995, filed Dec. 18, 1997, the contents of which are hereby incorporated by reference.

FIELD OF THE INVENTION

This invention relates to the field of sunflower-breeding and specifically to the hybrid sunflower variety PAN 9501.

BACKGROUND

Sunflower

Sunflower (*Helianthus annuus* L.) is one of the major annual crop species grown for edible oil. Others include soybean (*Glycine max* L.), peanut (*Arachis hypogaea* L.), rape or canola (Brassica spp.), and cotton (Gossypium spp.). The oil extracted from sunflower seeds is highly regarded by consumers in the United States due to its taste, cooking qualities, and fatty acid profile. See Heiser, C. B., 1978, *Taxonomy of Helianthus and Origin of Domesticated Sunflower,* IN Sunflower Science and Technology, American Society of Agronomy, Madison, Wis.

A dicot, sunflower is a member of the family Compositae and usually bears seeds on a single terminal head. It is distinguished from all other cultivated plants by its single stem and large inflorescence. See Knowles, P. F., 1978, *Morphology and Anatomy,* IN Sunflower Science and Technology. American Society of Agronomy, Madison, Wis. Sunflower and another member of its genus, Jerusalem artichoke (*H. tuberosus* L.), are also distinct in that they are the only important food plants domesticated in prehistoric times in the portion of North America which has become the United States.

In the United States, hybrid sunflower seeds are typically produced by seed companies and sold to farmers. On farms, hybrid sunflowers are usually grown as a row crop. During the growing season herbicides are widely used to control weeds; fertilizers are used to maximize yields; and fungicides and insecticides are used to control disease pathogens and insect pests. At maturity in the fall, sunflower seeds are usually harvested with a combine. From farms, harvested sunflower seeds are transported to crushing plants, where the edible oil is extracted therefrom. The edible oils are then sold to consumers, used in preparing food products, or serve as raw materials for other industrial uses.

While the agronomic performance of sunflower hybrids has improved, there is always a need to develop better hybrids with increased seed and oil yields. Moreover, heat and drought stresses and continually changing insect predators and disease pathogens present hazards to farmers as they grow sunflower hybrids. Thus, there is a continual need for sunflower hybrid varieties which offer higher seed yields and oil percentages in the presence of heat, drought, pathogens, and insects.

Inbred Lines and Hybrid Varieties

The ultimate purpose for developing sunflower inbred lines is to be able to dependably give rise to hybrids. Commercially viable sunflower hybrids, like hybrids in many other crop species, manifest heterosis or hybrid vigor for one or more economic traits.

Plants resulting from inbreeding, usually self-pollination (selfing), for several generations are termed inbred lines (inbreds). These inbreds are homozygous at almost all gene loci. When selfed, these inbreds produce a genetically uniform population of true breeding inbred progeny. These inbred progeny possess genotypes and phenotypes essentially identical to that of their inbred parent. A cross between two different inbreds produces a genetically uniform population of hybrid $F_1$ plants which are heterozygous for many gene loci. By contrast, a cross of two plants, which are not inbreds and are themselves heterozygous at a number of gene loci, will produce a population of progeny which are heterozygous at many loci but which are not genetically uniform.

The significance of this phenomenon is two-fold. First, seed supplies of inbreds may be maintained by selfing the inbreds. Equivalently, seed supplies of inbreds may be increased by growing inbred plants in isolation such that only pollen from that inbred genotype is available for fertilization during flowering (anthesis). Second, because the inbred lines themselves are genetically uniform, hybrids from inbred parents always have the same appearance and uniformity and can be produced by crossing the same set of inbred lines whenever desired. Thus, a hybrid created by crossing a defined set of inbreds will always be the same. Moreover, once the inbreds which give rise to a superior hybrid have been identified, a continual supply of the hybrid seed can be produced using these inbred parents.

Pollen Control

Commercial sunflower hybrids are typically produced by crossing two inbred lines. In order to effect such a cross the pollen-producing portion of the inflorescence from one of the inbred lines must either be removed or otherwise rendered sterile. Sunflower inflorescences are perfect and thus possess both stamens and pistils therein. Thus, hand or mechanical emasculation is not economically feasible for commercial hybrid production. However, several options for controlling male fertility are available. These options include cytoplasmic-genetic male sterility, genetic male sterility, and gametocides.

Hybrid sunflower seed is typically produced by a cytoplasmic-genetic male sterility system (CMS). This system requires both a homozygous nuclear locus and a cytoplasmic factor for sterility. Otherwise, the plant will produce viable pollen. The CMS requires A-lines (females), B-lines (maintainers), and R-lines (males). A-lines are homozygous for a nuclear allele for pollen sterility and possess a cytoplasmic factor for pollen sterility as well. A-lines are thus male-sterile. B-lines are homozygous for the sterile nuclear allele, but possess a fertile cytoplasmic factor. B-lines produce viable pollen. Moreover, B-lines usually have a nuclear genome essentially identical to a complimentary A-line. R-lines are homozygous for a fertile nuclear allele and possess a fertile cytoplasmic factor. Thus, R-lines produce viable pollen. Seed of A-lines is increased by pollinating A-line plants with pollen from complimentary B-lines. The resulting seed from A-lines pollinated with pollen from B-lines is also male-sterile because the fertile cytoplasmic factor from B-lines is not transmitted by pollen. Hybrid seed is produced by pollinating A-line plants with pollen from R-line plants. The resulting hybrid seeds are heterozygous at the nuclear locus and possesses the sterile cytoplasmic factor. Thus, the hybrid seed will grow into plants which produce viable pollen.

In commercial hybrid seed production, alternate strips of a female and a male inbred variety are planted in a field. Provided that there is sufficient isolation from sources of foreign pollen, inflorescences of the female inbred (A-line) will be fertilized only by pollen from the male inbred (R-line). If so, the resulting seed is exclusively a single hybrid. Often a hive of bees is placed near the production field to ensure that sufficient bees are present to effect pollination.

Plant Breeding

The use of male-sterile inbreds is but one factor in the production of sunflower hybrids. The development of sunflower hybrids also requires the development of homozygous inbred lines, the crossing of these lines to form hybrid seed, and the agronomic evaluation of the hybrids. Thus, breeding programs combine the genetic backgrounds from two or more inbred lines or various other broad-based germplasm sources into breeding pools from which new inbred lines are developed by selfing and selection for desired phenotypes. The newly developed inbreds are crossed with other inbred lines. The hybrids from these crosses are then evaluated to determine which have commercial potential.

Thus, the invention of a new hybrid sunflower variety involves a number of steps. These steps broadly include:

(1) selecting plants from germplasm pools for initial breeding crosses;

(2) crossing the selected plants in a mating scheme to effect breeding crosses;

(3) selfing and selecting progeny from the breeding crosses for several generations to produce a series of newly developed inbred lines, which, although different from each other, breed true and are highly uniform;

(4) crossing the newly developed inbred lines with other unrelated inbred lines to produce hybrid seeds; and (5) evaluating the hybrids in performance trials to determine their value as new commercial varieties.

During the inbreeding process, the vigor of the lines typically decreases to some extent. However, vigor is restored when two different inbred lines are crossed to produce the hybrid progeny.

Aside from the complexities of the choices in the above steps, there are many important factors to be considered in the art of plant breeding. These factors include the breeder's ability to recognize important morphological and physiological characteristics, the ability to design evaluation techniques for genotypic and phenotypic traits of interest, and the ability to search out and exploit the genes for the desired traits in new or improved combinations.

The objective of commercial sunflower hybrid development programs is thus to develop new inbred lines. These new lines are then used to produce hybrids which, in turn, produce high seed and oil yields in the presence of environmental hazards. The primary trait sunflower breeders seek to improve is either total seed yield or total oil yield. However, many other major agronomic traits are of importance in hybrid combination and have an impact on yield. Such traits include percent moisture at harvest, percent oil in harvested seeds, plant height, test weight, days to flower, days to maturity, resistance to stalk breakage, resistance to lodging, seed quality, and resistance or tolerance to temperature and moisture stress and to disease pathogens and insects.

The inbred lines per se must also have acceptable performance levels for parental traits such as seed yields, seed sizes, and pollen production. All of these traits affect the ability of a parental line to produce seed in economically sufficient quantities. Many if not all of these traits are affected by several genes.

Pedigree Breeding

The pedigree method of breeding is a widely used methodology for new line development. Generally this procedure involves crossing two or more inbred parent lines to produce an $F_1$ generation, then self-pollination of the $F_1$ generation to produce the $F_2$ generation. The $F_2$ generation and subsequent progeny segregate for all traits in which the inbred parent lines differ. An example of the process in which an $F_2$ generation is present is set forth below. Variations of this generalized pedigree method are used. However, all variations produce a segregating generation which contains a range of variation for the traits in which the inbred parents differ.

EXAMPLE 1

Hypothetical Example of Pedigree Breeding Program
Consider a cross between two inbred lines which
differ for alleles at six loci.
The parental genotypes are:

| Parent 1 | AbCdeF/AbCdeF |
| Parent 2 | aBcDEf/aBcDEf |

The $F_1$ from a cross between these two parents has the genotype:

| $F_1$ | AbCdeF/aBcDEf |

Selfing the $F_1$ will produce an $F_2$ generation which includes the following genotypes:

AbcDEf/abCdeF
AbcDef/abCdEF
AbcDef/abCdeF
.
.
.

The number of possible genotypes in the $F_2$ generation is $3^6$ (=729). But the $F_2$ generation will produce only $(2^6)-2$ (=62) possible new inbreds. However, only a very limited proportion of these combinations will be useful. Thus, only a very small proportion of the progeny from $F_2$ individuals can give rise to progeny possessing these new and useful allelic combinations.

It has been shown that many traits of economic value in sunflowers are under the genetic control of multiple genetic loci, and that there are a large number of unique combinations of these genes present in sunflower germplasm. Fick, G. N., 1978, *Breeding and Genetics,* IN Sunflower Science and Technology, American Society of Agronomy, Madison, Wis.

By way of example, if one assumes the number of segregating loci in an $F_2$ generation to be somewhere between 20 and 50 and one further assumes that each parent is fixed for half of the favorable alleles present, it is then possible to calculate approximate probabilities of producing an inbred which has a favorable allele at $\{(n/2)+m\}$ loci, where $n/2$ is the number of favorable alleles in each of the parents and m is the number of additional favorable alleles in the new inbred. See Probability of Developing an Inbred With m of n Favorable Alleles, below. The number m is assumed to be greater than three because each allele has such a small effect that evaluation techniques are not sensitive enough to detect differences due to three or fewer favorable alleles. The probabilities in the Example below are the probabilities that at least one genotype with $(n/2)+m$ favorable alleles will occur.

Probability of Developing an Inbred With m of n Favorable Alleles

Assume each parent has $n/2$ of the favorable alleles and only ½ of the combinations of loci are economically useful.

| No. of segrega-ting loci (n) | No. of favorable alleles in Parents (n/2) | No. of favorable alleles in new inbred (n/2) + m | Probability that genotype occurs* |
|---|---|---|---|
| 20 | 10 | 14 | $3 \times 10^{-5}$ |
| 24 | 12 | 16 | $2 \times 10^{-5}$ |
| 28 | 14 | 18 | $1 \times 10^{-5}$ |
| 32 | 16 | 20 | $8 \times 10^{-6}$ |
| 36 | 18 | 22 | $5 \times 10^{-6}$ |
| 40 | 20 | 24 | $3 \times 10^{-6}$ |
| 44 | 22 | 26 | $2 \times 10^{-6}$ |
| 48 | 24 | 28 | $1 \times 10^{-6}$ |

*Probability that a useful combination exists does not include the probability of identifying this combination if it does occur.

As can be seen from above, these probabilities are on the order of $10^{-5}$ or smaller. The probability of being able to identify this improved combination (genotype) based on replicated field testing would most likely be smaller than these values. The probability of being able to identify an improved genotype by replicated performance trials is a function of the population size of genotypes tested and how testing resources are allocated in the testing program.

SUMMARY OF THE INVENTION

According to the invention, there is provided a hybrid sunflower plant, PAN 9501, produced by crossing two sunflower inbred lines. The present invention thus relates to the hybrid seed PAN 9501, the hybrid plant produced from the seed, and variants, mutants, and other modifications of hybrid PAN 9501.

According to the invention there is provided a hybrid sunflower seed including the substantial phenotype of PAN 9501. There is also provided a hybrid sunflower plant arising from the hybrid sunflower seed, the plant including the substantial phenotype of PAN 9501. There is further provided a regenerable tissue from the hybrid sunflower seed designated PAN 9501 or from the hybrid sunflower plant arising from the seed and a plant arising from the regenerable tissue. There is still further provided a callus arising from the regenerable tissue and a plant regenerated from the callus.

There is provided a process of producing a hybrid sunflower seed designated PAN 9501 from a first inbred and a second inbred including the step of planting a seed of the first inbred such that a first inbred plant will germinate therefrom, the first inbred developing a female inflorescence, the female inflorescence being pollinated by pollen from the second inbred, the hybrid sunflower seed developing from the pollinated female inflorescence.

The process may include the step of planting a seed of the second inbred in proximity to the planted seed of the first inbred, such that a second inbred plant will germinate therefrom, the second inbred plant developing a male inflorescence, a quantity of pollen arising from the male inflorescence and such that the quantity of pollen from the second inbred plant is transmitted to the female inflorescence of the first inbred.

The process may further include planting the seed of the second inbred in proximity to the planted seed of the first inbred such that the pollen from the second inbred is transmissible to the female inflorescence of the first inbred by insects or more specifically by bees.

The process may still further include the step of harvesting the hybrid sunflower seed.

The process may yet further include means for preventing viable pollen from the first inbred from pollinating the female inflorescence of the first inbred, the means selected from the group of practices consisting of emasculating the first inbred, introgressing cytoplasmic-genetic male sterility into the first inbred, introgressing genetic male sterility into the first inbred, applying a gametocide to the first inbred and combinations thereof.

A process of producing a sunflower seed is provided, the process including the steps of providing a hybrid sunflower plant with the substantial phenotype of PAN 9501, a gamete arising therefrom, and fertilizing the gamete such that a seed arises from the fertilized gamete. This process includes a gamete which is an egg cell or a sperm nucleus.

According to the invention there is also provided a sunflower zygote arising from a fertilization event, the fertilization event a union of a first gamete and a second gamete, the first gamete arising from a hybrid sunflower plant with the substantial phenotype of PAN 9501. The first gamete may be an egg cell or a sperm nucleus. There is also provided a sunflower seed arising from the zygote and a sunflower plant arising from the sunflower seed.

DEFINITIONS

Terms

1. Substantial phenotype. The phenotype of hybrid sunflower PAN 9501 as herein described, including minor modifications and variations which do not affect the agronomic performance or the end use properties thereof and referring to the hybrid sunflower seed, the hybrid sunflower plant germinating and growing from the hybrid sunflower seed, and all tissues therefrom.

2. Regenerable tissue. Tissue arising from the hybrid sunflower seed or the hybrid sunflower plant designated and described herein as PAN 9501, which is capable of being regenerated directly into plants or of being cultured into callus, the callus then being regenerated into plants.

3. Embryogenesis. The process of initiation and development of bipolar plant structures from either zygotic cells, somatic cells, or callus cells.

4. Callus. Undifferentiated tissue usually cultured in vitro on a synthetic medium.

5. Inbred, inbred line, or inbred parent. A relatively true breeding strain resulting from successive generations of inbreeding, such as self-pollination or from successive generations of backcrossing to a recurrent parent until the phenotype of the recurrent parent is substantially recovered and the trait from the donor parent is present.

6. Hybrid or hybrid variety. First-generation ($F_1$) progenies from a cross between two inbred lines, between two hybrids, or between a hybrid and an inbred line.

Agronomic Traits

1. SEED YIELD (OR YIELD) (LBS./A). Seed yield in pounds per acre adjusted to a basis of 10 percent moisture.

2. PCT. OIL (10%). Percent oil of harvested seeds, adjusted to a basis of 10 percent moisture.

3. OIL YIELD (LBS/A). Pounds of oil per acre. Calculated by multiplying seed yield by the percent oil then dividing by 100.

4. HEIGHT (IN). Average plant height (in). The average distance from the base of the stem to the base of the inflorescence (head or capitulum) of a genotype.

5. DAYS TO FLOWER-MID. The average length of time in days from emergence until fifty percent of the plants of a genotype begin anthesis. Anthesis begins when the outer whorl of disk flowers have opened.

5a. DAYS TO FLOWER, FIRST. The average length of time in days from emergence until the first plant of a genotype begins anthesis.

6. SEED MOISTURE (%). The average percent moisture of the harvested seed for a genotype.

7. LODGING (%). The average percentage of plants at harvest time in which the stems are tilting from the vertical at an angle of more than fifteen degrees.

8. TEST WEIGHT (LBS/BU). Test weight in pounds per bushel. The bulk density of the harvested seeds (achenes) of a genotype.

9. NECK BREAK (%). The percentage of plants at harvest time with broken necks, a neck being the internode extending between the head and the nearest stem node basal to the head.

Morphological Traits

1. Class. Oil or non-oil type (confectionery).
2. Maturity
   a. Days to Head. Number of days from emergence to the first visible appearance of the first head of fifty percent of the plants of a genotype.
   b. Days to Harvest Ripeness. Number of days from emergence to harvest ripeness of fifty percent of the plants of a genotype. Harvest ripeness occurs when the moisture level of the head is sufficiently low that it may be mechanically harvested.
   c. Comparative Days to Head. Comparative number of days from emergence to the first visible appearance of the first head of fifty percent of the plants of a genotype.*
   d. Comparative Days to Harvest Ripeness. Comparative number of days to harvest ripeness.*
3. Height
   a. Height. Height (cm) at harvest ripeness. The average distance from the base of the stem to the base of the inflorescence (head or capitulum) of a genotype.
   b. Comparative Height. Comparative height (cm) at harvest ripeness. The average distance from the base of the stem to the base of the inflorescence (head or capitulum) of a genotype as compared to the height of the comparison variety.*
4. Stem
   a. Internode Length. Length (cm) of the adjacent internode basal to the head at harvest ripeness.
   b. Leaf Number. Number of leaves at harvest ripeness.
   c. Comparative Internode Length. Comparative internode length (cm) at harvest ripeness.*
   d. Comparative Leaf Number. Comparative number of leaves at harvest ripeness.*
   e. Branching Habit. Branching habit at harvest ripeness: e.g. no branching, top branching (with central head), basal branching or fully branched (without central head).
   f. Growing Point Color. Color of the growing point during active growth and development, e.g. green or yellow.
5. Leaves (midstem at flowering)
   a. Blade Length. The length of a leaf blade from the leaf base to the leaf tip, excluding the petiole (cm).
   b. Blade Width. The maximum width of a leaf blade (cm).
   c. Comparative Blade Length.* The comparative length of a leaf blade from the leaf base to the leaf tip, excluding the petiole (cm).
   d. Comparative Blade Width.* The comparative maximum width of a leaf blade (cm).
   e. Width-Length Ratio. Narrower than long, equal, or wider than long.
   f. Leaf Shape. Cordate or other.
   g. Leaf Apex. Acuminate or other.
   h. Leaf Base. Auriculate or truncate.
   i. Leaf Margin. Entire, finely crenate, coarsely crenate, or other.
   j. Depth of Margin Indentations. Shallow, intermediate, or deep.
   k. Attitude. Erect, ascending, horizontal, or descending.
   l. Surface. Smooth, crinkled (ridged), or other.
   m. Color. Color of leaf, e.g. light-green, green, dark-green, or brown.
   n. Margin Color. Color of leaf margin, e.g. green or yellow.
6. Head (at flowering)
   a. Ray Flowers. Absent or present.
   b. Ray Flower Color. Yellow, sulfur-yellow, orange-yellow, or other.
   c. Disk Flower Color. Yellow, red, or purple.
   d. Anthocyanin in Stigmas. Absent or present.
   e. Pollen Color. White (colorless) or yellow.
   f. Pappi. Green or rust (red).
   g. Ray Length (mm).
   h. Comparative Ray Length (mm).*
   i. Ray Width (mm).
   j. Comparative Ray Width (mm).*
7. Head (at seed maturity)
   a. Diameter (cm).
   b. Comparative Diameter (cm).*
   c. Receptacle Shape. Flat, convex or concave.
   d. Head Attitude. Attitude of the head, e.g. vertical (erect), ascending, horizontal, or descending.
   e. Seeds per Head. Number of seeds per head.
   f. Comparative Seeds per Head.*
8. Seeds.
   a. Outer Pericarp. Clear, stripped black, or nearly solid black.
   b. Middle Pericarp. White or solid purple.
   c. Inner Pericarp (seed coat). No color or brownish-black.
   d. Stripes. Absent, even black and white stripes, broad black and narrow white, black with narrow dark gray stripping, or other.
   e. Mottling. Absent or present.
   f. Shape. Ovate, obovate (shield), narrowly obovate, oblong, or elliptic.
   g. Shape (cross-section). Not curved or curved.
   h. Length (mm).
   i. Comparative Length (mm).*
   j. Seed Weight (g/100 seeds).
   k. Comparative Seed Weight (g/100 seeds).*
   l. Seed Size Fraction. Percent seed held on 7.9 mm ($^{20}/_{64}$ inch) round-hole screen.
   m. Comparative Seed Size Fraction. Percent seed held on 7.9 mm ($^{20}/_{64}$ inch) round-hole screen.*
9. Disease Reactions.
   a. Rust (*Puccinia helianthi* Schw.). Resistant, susceptible, or unknown (specified as to race).
   b. Downey Mildew (*Plasmorpara halstedii*). Resistant, susceptible, or unknown.

10. Insect Reactions
   a. Sunflower Seed Midge (*Contarinia schulzi* (Gagne)).
      i. Average Midge Damage Rating. The average midge damage rating in one or a serial of trials per a 0–5 scale; 0 being no damage and 5 being no seeds present. (based on Bracken, G. K. 1991. Can. J. Plant Sci 71:81–85, incorporated herein by reference.)
      iii. Relative Midge Damage Rating. The Average Midge Damage Rating for a genotype in one or a series of trials, divided by the average damage rating of all genotypes in the one or series of trials. A value less than one indicates a damage rating less than the trial average.
*, as compared to a check variety (genotype).

EXAMPLE 1

Obtaining Harvested Sunflower Oil Seeds from PAN 9501 Hybrid Sunflower Seed

In practice, PAN 9501 hybrid sunflower seed is planted at a depth sufficient to place the seeds in moist soil and such that hybrid seedlings growing therefrom can emerge. During the growing season, herbicides, fertilizers, insecticides and fungicides are applied as is well known in the art. Moreover, weeds are usually controlled by mechanical techniques. When the hybrid sunflowers are mature, they are usually harvested by a combine. Harvested seed from the hybrid sunflowers is usually sold and transported to a facility where the sunflower oil is extracted.

Detailed Description of the Invention

PAN 9501 is a sunflower hybrid which may be described as follows. However, additional agronomic data and morphological descriptors may also further describe PAN 9501. Thus, the following agronomic performance data and morphological descriptions are by way of illustration, not limitation.

EXAMPLE 2. MORPHOLOGICAL DESCRIPTION OF PAN 9501.
Morphological Description of
Hybrid Sunflower PAN 9501*
Check Variety: CMS HA89/RHA274

1. Class: Oil Type

2. Maturity:

| | | |
|---|---|---|
| a. Days to Head | 56 | |
| b. Days to Harvest Ripeness | 99 | |
| c. Comparative Days to Head ** | 3 days later | |
| d. Comparative Days to Harvest Ripeness ** | 4 days later | |

3. Height:

| | |
|---|---|
| a. Height | 170 cm |
| b. Comparative Height ** | 12 cm taller |

4. Stem

| | |
|---|---|
| a. Internode Length | 5.56 cm |
| b. Leaf Number | 31 |
| c. Comparative Internode Length ** | 0.27 cm longer |
| d. Comparative Leaf Number ** | 0 (same) |
| e. Branching Habit | No branching |
| f. Growing Point Color | Green |

5. Leaves (midstem at flowering)

| | |
|---|---|
| a. Blade Length | 20.0 cm |
| b. Blade Width | 18.0 cm |
| c. Comparative Blade Length ** | 1.4 cm longer |
| d. Comparative Blade Width ** | 3.0 cm wider |
| e. Width-Length Ratio | Narrower than long |
| f. Leaf Shape | Cordate |
| g. Leaf Apex | Acuminate |
| h. Leaf Base | Truncate |
| i. Leaf Margin | Other |
| j. Depth of Margin Indentations | Deep |
| k. Attitude | Descending |
| l. Surface | Crinkled |
| m. Color | Green |
| n. Margin Color | Green |

6. Head (at flowering)

| | |
|---|---|
| a. Ray Flowers | Present |
| b. Ray Flower Color | Yellow |
| c. Disk Flower Color | Yellow |
| d. Anthocyamins in Stigmas | Absent |
| e. Pollen Color | Yellow |
| f. Pappi | Green |
| g. Ray Length | 74.2 mm |
| h. Comparative Ray Length * | 1.4 mm longer |
| i. Ray Width | 18.7 mm |
| j. Comparative Ray Width * | 1.9 mm wider |

7. Head (at seed maturity)

| | |
|---|---|
| a. Diameter | 14.2 cm |
| b. Comparative Diameter ** | 0.6 cm wider |
| c. Receptacle Shape | Convex |
| d. Head Attitude | Descending |
| e. Seeds per Head | 1287 |
| f. Comparative Seeds per Head ** | 8 seeds less |

8. Seeds

| | |
|---|---|
| a. Outer Pericarp | Striped Black |
| b. Middle Pericarp | White |
| c. Inner Pericarp | No Color |
| d. Stripes | Broad Black and Narrow White |
| e. Mottling | Present |
| f. Shape | Obovate |
| g. Shape (cross-section) | Curved |
| h. Length | 11.0 mm |
| i. Comparative Length ** | 0.3 mm shorter |
| j. Seed Weight | 5.5 g |
| k. Comparative Seed Weight ** | 1.3 g heavier |
| l. Seed Size Fraction | 0.0% |
| m. Comparative Seed Size Fraction ** | Same |

9. Disease and Insect Reactions

| | |
|---|---|
| a. Rust | |
|   Race 1 | Resistant |
|   Race 2 | Resistant |
|   Race 3 | Resistant |
| b. Downy Mildew | Resistant |

10. Insect Reactions ***

| | |
|---|---|
| a. Sunflower Seed Midge | |
|   i. Average Midge Damage Rating | 1.6 (3.4)+ |
|   ii. Relative Midge Damage Rating | 0.57 (1.42) |

Based on observations taken at Philo, Illinois and at Brookings and Huron, South Dakota, in 1996 crop year.
* As compared to check variety.
** Based on values reported in Bergland, D, 1997, North Dakota Hybrid Sunflower Performance Testing. NDSU Extension Service Publication A-652 (Revised), the entire contents of which are hereby incorporated by reference.
Values in parentheses are those of the check variety.

Compared to the check variety (CMS HA89/RHA274), PAN 9501 heads later; attains harvest ripeness later; is taller, has a greater internode length, leaf blade width, leaf blade length, ray width and ray length and lower average and relative midge damage ratings. PAN 9501 also has a slightly wider head diameter and fewer seeds per head than the check variety. Harvested seeds of PAN 9501 are somewhat shorter and heavier.

commercial hybrids and was significantly lower in percent oil. PAN 9501 was significantly later flowering (first and mid-flowering) than all commercial checks except DeKalb EXAMPLE 3. AGRONOMIC PERFORMANCE OF PAN 9501.
AGRONOMIC DATA OBTAINED FROM TESTING
PAN 9501 AT 8 U.S. LOCATIONS IN 1996

| HYBRID | SEED YIELD[1] | | PCT. OIL (10%) | OIL YIELD (LBS/A) | DAYS TO FLOWER | | SEED MOISTURE (%) | HEIGHT (IN) | TEST WEIGHT (LBS/BU) |
|---|---|---|---|---|---|---|---|---|---|
| | LBS/A | RANK | | | FIRST | MID | | | |
| LOCATIONS | 8 | | 8 | 8 | 5 | 5 | 6 | 6 | 1 |
| PAN 501 | 2517 | 2 | 39.9 | 1104 | 67 | 71 | 13.4 | 67 | 30.3 |
| CARGILL 187 | 2035 | 28 | 41.0 | 834 | 63 | 68 | 12.6 | 62 | 29.2 |
| CARGILL 270 | 4999 | 31 | 42.0 | 840 | 63 | 67 | 11.8 | 61 | 30.5 |
| LB 3790 | 1996 | 32 | 43.4 | 866 | 64 | 69 | 12.0 | 65 | 33.6 |
| LB 3904 | 2074 | 25 | 42.0 | 871 | 66 | 70 | 13.5 | 67 | 29.3 |
| | 2139 | | 40.9 | 894 | 66 | 70 | 13.4 | 67 | 30.3 |
| C.V.(%) | 16 | | 6 | 19 | 3 | 3 | 16 | 7 | 3 |
| LSD (0.2) | 103 | | 1.0 | 73 | 1 | 1 | 0.7 | 2 | 0.5 |

Analysis of Variance for Seed Yield and Moisture at harvest used replication data from each location. Analysis of Variance of all her traits was based on location means.

PAN 9501 was evaluated in performance trials at eight locations in 1996. Agronomic character means for PAN 9501, Cargill 187 and three other commercially available sunflower hybrids are depicted in the first table of Example 3. Cargill 187 is presently one of the most widely grown sunflower hybrids in the United States and is generally viewed by persons skilled in the art as high yielding (seed yield) and with good yield stability over a range of environments. The oil percentage of harvested seed of Cargill 187 is viewed as being low to average. Cargill 187 is perceived as a short sunflower hybrid, with average lodging and is considered to be medium to late in flowering.

3904. The mean seed moisture percentage of PAN 9501 was significantly higher than Cargill 187, Cargill 270 and DeKalb 3790 and not significantly different from that of DeKalb 3904. The height of PAN 9501 was significantly taller than Cargill 187 and Cargill 270 and not significantly different than those of DeKalb 3790 and DeKalb 3904. The mean test weight of PAN 9501 was significantly less than that of DeKalb 3790, significantly greater than those of Cargill 187 and DeKalb 3904 and not significantly different than the test weight of Cargill 270.

AGRONOMIC DATA OBTAINED FROM TESTING
PAN 9501 IN 1995 AND 1996 at U.S. LOCATIONS

| | SEED YIELD[1] (LBS/A) | PCT. OIL (10%) | OIL YIELD (LBS/A) | MOISTURE (%) | DAYS TO FLOWER -MID | HEIGHT (IN) | LODGING (%) | TEST WEIGHT (LBS/BU) |
|---|---|---|---|---|---|---|---|---|
| NS | 14 | 14 | 14 | | | | | |
| | 2317 | 40.8 | 960 | | | | | |
| 187 | 2080 | 41.8 | 891 | | | | | |
| | 2223 | 41.3 | 927 | | | | | |
| | 19 | 4 | 19 | | | | | |
| | 138 | 0.6 | 58 | | | | | |
| NS | 12 | 12 | 12 | | | | | |
| | 2210 | 38.7 | 854 | | | | | |
| 187 | 2023 | 39.6 | 803 | | | | | |
| | 2067 | 39.4 | 813 | | | | | |
| | 11 | 5 | 13 | | | | | |
| | 79 | 0.7 | 38 | | | | | |
| NS | 26 | 26 | 26 | 14 | 11 | 17 | 13 | 11 |
| | 2266 | 39.8 | 909 | 11.6 | 65 | 66 | 17 | 28.4 |
| 187 | 2054 | 40.8 | 850 | 10.3 | 64 | 60 | 16 | 26.8 |
| | 2151 | 40.4 | 874 | 10.9 | 64 | 64 | 15 | 28.0 |
| | 16 | 5 | 17 | 19 | 4 | 7 | 59 | 9 |
| | 82 | 0.4 | 35 | 0.7 | 1 | 1 | 3 | 0.9 |

Analysis of Variance for Seed Yield and Moisture at harvest used replication data from each location. Analysis of Variance of all her traits was based on location means.

In this series of performance trials, PAN 9501 had significantly higher seed yields and oil yield per acre than all PAN 9501 was also evaluated in a different set of locations in 1995 and 1996, for a total of 26 sites. In all sites PAN 9501 was evaluated with Cargill 187. PAN 9501 had significantly higher seed and oil yields and significantly lower mean oil percentages than Cargill 187. Harvested seed of PAN 9501 were significantly higher in moisture and had significantly higher mean test weight than Cargill 187. Finally, PAN 9501 plants were significantly taller and later to flower, but there was no significant difference in percent lodging.

AGRONOMIC DATA OBTAINED FROM TESTING PAN 9501 AT U.S. LOCATIONS IN 1997

|  | SEED YIELD[1] (LBS/A) | PCT. OIL (10%) | MOISTURE (%) | DAYS TO FLOWER -MID* | HEIGHT (IN) | LODGING (%) | NECK BREAK (%) |
| --- | --- | --- | --- | --- | --- | --- | --- |
| LOCATIONS | 5 | 6 | 5 | 1 | 1 | 2 | 4 |
| PAN 9501 | 2618 | 43.1 | 15.3 | 35 | 65 | 0 | 7 |
| CARGILL 187 | 2309 | 41.7 | 12.7 | 31 | 55 | 2 | 6 |
| MEAN | 2278 | 42.8 | 13.3 | 33 | 65 | 2 | 7 |
| C.V. (%) | 13 | 7 | 11 | 3 | 4 | 103 | 1 |
| LSD (0.2) | 113 | 1.5 | 0.5 | 1 | 3 | 1 | 46 |

[1]Analysis of Variance for Seed Yield and Moisture at harvest used replication data from each location. Analysis of Variance of all other traits was based on location means.

*Days after July 1, 1997

PAN 9501 was evaluated in a set of six locations in 1997. However, yield and moisture data were not included from one of the six locations because of an unacceptably high CV. Yield, moisture, days to flower, height, and lodging means of PAN 9501 were significantly different than those of Cargill 187. Percent oil and percent neck break means of PAN 9501 and Cargill 187 were not significantly different.

AGRONOMIC DATA OBTAINED FROM TESTING PAN 9501 AT U.S. LOCATIONS IN 1998

|  | SEED YIELD[1] (LBS/A) | PCT. OIL (10%) | OIL YIELD (LBS/A) | MOISTURE (%) |
| --- | --- | --- | --- | --- |
| LOCATIONS | 5 | 1 |  | 5 |
| PAN 9501 | 2798 | 42.2 |  | 13.4 |
| CARGILL 187 | 2659 | 44.2 |  | 14.9 |
| MEAN | 2576 | 43.8 |  | 13.8 |
| C.V. (%) | 16 | 2.4 |  | 9.3 |
| LSD (0.2) | 156 | 0.9 |  | 0.5 |

[1]Analysis of Variance for Seed Yield and Moisture at harvest used replication data from each location. Analysis of Variance of all other traits was based on location means.

PAN 9501 was evaluated at five sites in 1998 with Cargill 187. The mean yield of PAN 9501 was not significantly different than that of Cargill 187. However, percent oil and percent moisture of seed harvested from PAN 9501 were significantly different than those of Cargill 187.

AGRONOMIC DATA OBTAINED FROM TESTING PAN 9501 AT 7 LOCATIONS IN 1992 AND 10 LOCATIONS IN 1993, ALL IN FRANCE

|  | SEED YIELD (Q/HA) | | | PCT. OIL (10%) |
| --- | --- | --- | --- | --- |
|  | 1992 | 1993 | % | 1992–1993 |
| LOCATIONS | 7 | 10 |  | 17 |
| Euroflor** | 29.8 | 29.1 |  | 49.5 |
| Viki** | 29.3 | 29.0 |  | 50.6 |
| PAN 9501 | 31.2 | 34.3 | 111.3* | 46.5 |

*Percent of two check varieties.
**Check variety.

PAN 9501 was evaluated in 1992 and 1993 by the French Ministry of Agriculture. PAN 9501 seed yields were higher than both checks in both years, out-yielding the average of the check varieties by 11.3% over both years. Oil percentage of PAN 9501 were lower than either check.

EXAMPLE 4

Regeneration of Plants by Tissue Culture of PAN 9501.

Plants may be regenerated by tissue culturing PAN 9501 as taught by Espinasse et al., Crop Science 29:201 (1989), the disclosure of which is incorporated by reference. Fertilized ovaries of PAN 9501 are extracted about four days after pollination, sterilized 10 minutes in a 0.282M NaOCl solution, and rinsed three times in sterile water for five minutes per rinsing. Regenerable tissues, such as embryos, are then aseptically excised from the fertilized ovaries and plated on at least two Murashige and Skoog (MS) media. From about 10 to 30 embryos are plated on each MS medium. Embryos should range from the early heart-stage ($\geq 2$ mm long without cotyledons) to the torpedo-stage ($\leq 1.2$ mm long with small cotyledons). After plating, petri dishes are sealed, for example with parafilm, and placed in a growth chamber with continuous cool white fluorescent lighting, and are maintained at 30°+5.0° C. Calli grow from the explanted embryos. The calli subsequently regenerate shoots. The regenerated shoots are transferred to a MS medium without hormones so that roots will develop therefrom. The regenerated plants with shoots and roots are then transferred to a medium, such as vermiculite, for subsequent growth in a greenhouse. These regenerated plants usually are fertile and can be selfed or crossed to other genotypes to produce viable seed.

Plants of PAN 9501 may also be regenerated by organogenesis by the protocol disclosed by Chraibi et al., A Genotype-Independent System Of Regeneration From Cotyledons Of Sunflower (*Helianthus annuus* L.). The Role Of Ethylene, Plant Science 86: 215–221 (1992a), the disclosure of which is hereby incorporated by reference. The foregoing organogenesis regeneration protocol disclosed by Chraibi et al. (1992a) results in high regeneration efficiencies which are independent of genotype used. Alibert et al., Sunflower Tissue And Cell Cultures And Their Use In Biotechnology. Plant Physiology and Biochemistry 32(1): 31–44 (1994). Mature hybrid PAN 9501 seeds may be surface-sterilized by immersion for about 20 minutes in a 5% (w/v) calcium hypochlorite solution containing about 0.1% of a surfactant such as Tween 20, then rinsed about 3 times in sterile distilled water. The seeds then may be germinated in culture tubes on hormone-free half-strength Murashige and Skoog (MS) medium for about 48 hours. MS medium is disclosed in T. Murashige and F. Skoog, A Revised Medium For Rapid Growth And Bioassays With Tobacco Tissue Cultures, Physiol. Plant. 15: 473–497 (1962), the entire contents of which are hereby incorporated by reference. Cotyledons from 2-day old seedlings may be excised and cut transversely into two pieces. The excised and transversely cut explants may be then cultured in 250 ml Erlenmeyer flasks containing about 100 ml of a full-strength liquid MS medium supplemented with 50 mM $KNO_3$, 1 mM inositol, 500 mg/l casein hydrosylate, 5 μM naphthaleneacetic acid (NAA), and 4.4 μM benzylaminopurine (BAP). All constituents may be added to the medium and the pH adjusted to about pH 5.7 before the medium is autoclaved at about 120° C. for 20 minutes as is known to the art.

The Erlenmeyer flasks containing the explants and supplemented liquid MS medium are maintained (incubated) in a rotary shaker at about 100 revolutions/min. After an incubation period ranging from about one to about 20 days in liquid MS medium, the explants are transferred to Petri dishes sealed with a removable sealing product such as Parafilm™ and containing about 10 ml of MS medium solidified by about 6 g/l agar until shoots develop therefrom. Cultures may be maintained at about 25° C.±1° C. under a 16-h light/8-h dark cycle with a light flux of about 100 μmol/m$^{-2}$ s$^{-1}$. An exemplary lamp with such an output is an OSRAM L36W/36™ (Nature tube).

Shoot cuttings about 10 mm in length may be excised from regenerating explants and transferred to containers containing half-strength MS medium supplemented with 2.7 μM NAA and 1.5 μM gibberellic acid (GA3), as disclosed by Chraibi et al. , Plant Cell Reports 10: 204–207 (1990), the entire contents of which are hereby incorporated by reference. When roots appear on the shoot cuttings, the resulting plantlets are transferred into pots containing a respective 4:2:1 mixture of peat moss: vermiculite: sand and incubated in a humidity-saturated atmosphere for about 1 week. Plants are then grown in a greenhouse at about 24° C. under natural lighting coupled to a 12/12 h light/dark cycle with a flux of about 150–200 μmol m$^{-2}$s$^{-1}$ from an exemplary lamp such as a HPLR400 Philips lamp.

Another exemplary protocol for regenerating plants from regenerable tissue is disclosed by Chraibi et al., Enhancement Of Shoot Regeneration Potential By Liquid Medium Culture From Mature Cotyledons Of Sunflower (*Helianthus annuus*, L.), Plant Cell Reports 10: 617–620 (1992b), the contents of which are hereby enclosed by reference.

EXAMPLE 5

Isozyme Genotypes of PAN 9501.

Isozyme genotypes of PAN 9501 were determined by methods known to the art and are depicted below.

| HYBRIDS | ACP | PGD | PH1 | IDH | PGM | EST (cal) | MDH | GDH | GOT | ADH | ACO | SKDH | CAT | DIA |
|---|---|---|---|---|---|---|---|---|---|---|---|---|---|---|
| 501 | 12 | 22 | 12 | 11 | 12 | 22 | A/C | 12 | N | 11 | 11 | 12 | L | A/C |
| A30DA | 22 | 11 | 22 | 11 | 11 | 55 | A | 22 | N | 11 | 22 | 22 | L | C |
| A89A | 22 | 22 | 22 | 11 | 11 | 22 | A | 11 | N | 11 | 11 | 22 | L | A |
| 01R | 22 | 22 | 22 | 11 | 11 | 22 | A | 11 | N | 22 | 11 | 22 | L | C |
| 74R | 99 | 22 | 22 | 11 | 22 | 22 | A | 11 | N | 22 | 11 | 22 | L | C |

The isozyme genotypes depicted above have the following abbreviations: ACP, Acid phosphatase; PGD, 6-Phosphogluconate dehydrogenase; PH1, Phosphohexose isomerase; IDH, Isocitrate dehydrogenase; PGM, Phosphoglucomutase; EST(cal), Esterase; MDH, Malate dehydrogenase; GDH, Glutamic dehydrogenase; GOT, Glutamate-oxaloacetate transaminase; ADH, Alcohol dehydrogenase; ACO, Aconitase; SKDH, Shikimate dehydrogenase; CAT, Catalase; DIA, Diaphorase. HA30DA, HA89A, P801R, and P274R are known standards.

EXAMPLE 6

AFLP™ Characterization of PAN 9501.
DNA Isolation

An exemplary DNA extraction buffer was prepared which included 500 mM NaCl, 100 mM Tris-HCl at a pH of 8.0, 50 mM EDTA, and 1.25% (w-v) SDS. Just prior to use, 0.38 g Sodium bisulfite/100 ml was added to the extraction buffer and the pH was adjusted to between 7.8 and 8.0 with NaOH.

Coleoptiles from 5 day old seedlings were ground to powder with liquid nitrogen in a well chilled mortar and pestle, the resulting powder from each sample was transferred to a chilled 1.5 ml tube, and 500 μl extraction buffer was added. The powder and extraction buffer from each sample was mixed, then heated and incubated at 65° C. between 20–30 minutes, the tubes being inverted every 5–10 minutes. 500 μl chloroform was added to the top of each tube, the tubes were subsequently vortexed 1 minute, and then centrifuged at 2800 rpm at 4° C. for 10 minutes. The upper phase of each tube was pipetted into another 1.5 ml tube. Addition of chloroform, centrifuging, and re-pipetting of each sample into another 1.5 ml tube was repeated until a clear upper phase was obtained. Two volumes of ice-cold 95% ethanol were added to each sample and mixed therewith to allow the DNA to precipitate over a period of between 1 and 12 hours at −20° C. Each precipitated DNA sample was removed with a pasteur pipette and transferred to a 1.5 ml tube. Cold 70% ethanol was added to each DNA sample and the DNA sample and 70% ethanol were shaken gently for 10–15 minutes. The tubes were then centrifuged for 5 minutes at 3000 rpm to pellet the DNA. Adding cold 70% ethanol, shaking, and centrifuging was repeated until the DNA was no longer discolored, then the ethanol was discarded and the tubes were inverted for 10 minutes to allow the DNA to air dry. 50 μl sterilized, double-distilled water was added to dissolve each DNA sample. The samples were subsequently incubated at 65° C. and gently inverted every 30–60 minutes or until the DNA was dissolved. Tubes containing dissolved DNA were centrifuged for 10 minutes at 300 rpm and the supernatant of each sample was transferred to a clean Eppendorf tube. The DNA concentration of each sample was determined using a known concentration standard on a 1% Agarose gel (1×TBE), the gel was stained with Ethidium bromide and visualized under UV.

AFLP™ Procedure

1. Restriction Digestion of Genomic DNA. An AFLP™ Procedure, based on the instruction manual supplied by Life Technologies, Inc. was followed. Proprietary materials were supplied from the AFLP™ Analysis System I, consisting of an AFLP™ Starter Primer Kit and an AFLP™ Core Reagent Kit, both supplied by Life Technologies, Inc., Gaithersburg, Md. 20884. Extracted genomic DNA of each sample was digested with restriction enzymes. 12.5 μl of extracted DNA (20 ng/μl), 5 μl reaction buffer, 2 μl EcoRI/MseI, and 5.5 μl distilled water were combined in a 1.5 ml microcentrifuge tube for a total volume of 25 μl. The reaction buffer included 50 mM Tris-HCl at a pH of 7.5 and 50 mM Mg-acetate. The EcoRI/MseI was added at a rate of 1.25 units/μl for each restriction enzyme in a solution including 10 mM Tris-HCl at a pH of 7.5 and 50 mM NaCl. The resulting DNA-restriction enzyme mixture was mixed, collected by brief centrifugation, and incubated for 2 hours at 37° C., then further incubated 15 minutes at 70° C. to inactivate the restriction endonucleases. Sample tubes were subsequently placed on ice and the contents of each tube were collected by brief centrifugation.

2. Ligation of Adapters. Each sample of digested DNA was combined with adapter ligation solution and T4 DNA ligase. The adaptor ligation solution contained EcoRI and MseI adapters, 0.4 mM ATP, 10 mM Tris-HCl at a pH of 7.5, 10 mM Mg-acetate, and 50 mM K-acetate. The T4 DNA ligase was present at a rate of 1 unit/μl in a solution containing 10 mM Tris-HCl at a pH of 7.5, 1 mM DTT, 50 mM KCl, and 50% glycerol (v/v). The digested DNA-adaptor ligation mixture was gently mixed and centrifuged at room temperature, then incubated at 20° C. for 2 hours. 10 μl of the ligated DNA was transferred to a 1.5 ml microcentrifuge tube and diluted with 90 μl double-distilled water.

3. Pre-amplification Reactions. 5 μl of each ligated, diluted template DNA sample was pipetted into a 0.2 ml thin-walled microcentrifuge tube along with 40 μl of one of six exemplary pre-amp primer combination mixtures, 5 μl 10×PCR buffer (plus Mg), and 1 μl Taq DNA polymerase (1 unit/μl) to attain a total volume of 51 μl per sample. Each sample was then mixed gently, centrifuged to collect the reaction, and overlaid with 2 drops of mineral oil. The six pre-amp primer combinations were: E-ACC+M-CAG (primer pair A), E-ACG+M-CTG (primer pair B), E-AGC+M-CAC (primer pair C), E-AGG+M-CTG (primer pair D), E-AGG+M-CAG (primer pair E), and E-ACC+M-CTG (primer pair F). Pre-amplification was performed at 94° C. for 30 seconds, 56° C. for 60 seconds, 72° C. for 60 seconds, for 20 cycles and a soak temperature of 4° C. 10 μl of each pre-amplification mixture obtained was transferred to a 1.5 ml microcentrifuge tube along with 90 μl double-distilled water and selectively amplified.

4. Selective Amplification. For non-radioactive detection, primers were not end-labelled with $P^{32}$. 18 μl of EcoRI primer was diluted with 32 μl distilled water. For each primer pair, the following components were added to a 1.5 ml microcentrifuge tube and labelled A: 5 μl diluted EcoRI primer and 45 μl MseI primer (containing dNTP) for a total volume (10 reactions) of 50 μl. The following components were added to another 1.5 ml microcentrifuge and subsequently labelled B: 79 μl distilled water, 20 μl 10×PCR buffer plus Mg, and 1 μl Taq DNA polymerase (5 units/μl) for a total volume (10 reactions) of 100 μl. Each AFLP™ amplification was assembled by combining 5 μl diluted template DNA from pre-amplification, 5 μl of mixture A and 10 μl of mixture B in a 0.2 ml thin-walled microcentrifuge tube. The reaction mixture was gently mixed, centrifuged to collect, and overlaid with 2 drops mineral oil. The following amplification procedure was used for selective amplification in a Corbett Research PC-960C Cooled Thermal Cycler:

| No. | ° C. | Time(s) | ° C. | Time(s) | ° C. | Time(s) | No. Cycles |
|---|---|---|---|---|---|---|---|
| 1 | 94 | 60 | 65 | 60 | 72 | 90 | 1 |
| 2 | 94 | 60 | 64 | 60 | 72 | 90 | 1 |
| 3 | 94 | 60 | 63 | 60 | 72 | 90 | 1 |
| 4 | 94 | 60 | 62 | 60 | 72 | 90 | 1 |
| 5 | 94 | 60 | 61 | 60 | 72 | 90 | 1 |
| 6 | 94 | 60 | 60 | 60 | 72 | 90 | 1 |
| 7 | 94 | 60 | 59 | 60 | 72 | 90 | 1 |
| 8 | 94 | 60 | 58 | 60 | 72 | 90 | 1 |
| 9 | 94 | 60 | 57 | 60 | 72 | 90 | 1 |
| 10 | 94 | 60 | 56 | 60 | 72 | 90 | 1 |
| 11 | 94 | 30 | 56 | 30 | 72 | 60 | 23 |

Total Time: 3 h, 18 min.

Gel Analysis. After selective amplification each sample was combined with volume (20 μl) of formamide dye (98% formamide, 10 mM EDTA, enol blue, xylene cyanol) and the mixtures were heated for 3 minutes at and immediately placed on ice. A 6% polyacrylamide gel was prepared (20:1 de: BIS; 7.5 M urea; 1×TBE). Pre-electrophoresis was at constant power (55 20 minutes. 6 μl of each sample was loaded into one lane of the gel and oresis was conducted at constant power until the xylene cyanol (slower ⅔ down the length of the gel. The gel was subsequently silver stained to the resulting bands.

6. The silver stained gel image was captured on a UVP gel documentation system using UVP Grabit software. Banding patterns were analyzed using the software, Gene Tools from SynGene, to obtain the information summarized in the table.

| No. | Mol. Weight | Height | Raw Vol. | Mol. Weight | Height | Raw Vol. | Mol. Weight | Height | Raw Vol. |
|-----|------------|--------|----------|------------|--------|----------|------------|--------|----------|
| 1 | 338.77 | 27.14 | 1267.03 | 326.09 | 41.54 | 1633.72 | 341.20 | 16.53 | 1113.92 |
| 2 | 334.76 | 50.82 | 3460.64 | 307.95 | 82.57 | 7627.59 | 331.58 | 14.33 | 1716.88 |
| 3 | 303.58 | 20.48 | 731.49 | 303.58 | 63.19 | 3450.63 | 324.54 | 26.79 | 1205.27 |
| 4 | 297.13 | 32.31 | 1462.12 | 294.31 | 65.15 | 4902.15 | 281.27 | 16.86 | 912.56 |
| 5 | 256.01 | 13.33 | 407.00 | 288.08 | 37.44 | 3066.41 | 277.94 | 24.95 | 1106.12 |
| 6 | 272.69 | 17.86 | 381.27 | 279.27 | 67.86 | 5357.47 | 264.99 | 19.17 | 2113.75 |
| 7 | 266.90 | 33.43 | 1831.94 | 264.36 | 64.26 | 7585.13 | 243.77 | 61.31 | 6834.58 |
| 8 | 255.07 | 38.72 | 2065.56 | 252.65 | 48.26 | 3205.88 | 234.65 | 43.51 | 3692.61 |
| 9 | 242.04 | 28.75 | 1915.45 | 235.21 | 46.27 | 5074.53 | 225.86 | 13.45 | 647.54 |
| 10 | 229.67 | 30.82 | 3638.78 | 231.32 | 41.57 | 2723.37 | 222.66 | 34.70 | 2082.78 |
| 11 | 221.60 | 12.84 | 722.64 | 225.86 | 18.57 | 1145.77 | 216.89 | 32.58 | 2415.89 |
| 12 | 213.30 | 16.05 | 716.30 | 193.24 | 21.80 | 1322.70 | 209.27 | 41.91 | 4611.23 |
| 13 | 206.79 | 24.81 | 1570.60 | 187.88 | 22.77 | 1326.04 | 195.67 | 20.12 | 1241.43 |
| 14 | 200.48 | 27.94 | 1899.19 | 182.09 | 18.39 | 966.63 | 178.71 | 15.71 | 1404.84 |
| 15 | 193.84 | 28.56 | 1751.72 | 168.40 | 22.84 | 1158.04 | 131.61 | 10.83 | 595.37 |
| 16 | 186.70 | 15.89 | 751.53 | 158.19 | 15.72 | 1085.28 | 119.70 | 14.67 | 1271.43 |
| 17 | 177.04 | 40.74 | 3931.79 | 153.32 | 36.64 | 2108.16 | | | |
| 18 | 157.70 | 27.96 | 3441.20 | 131.61 | 18.72 | 2004.58 | | | |
| 19 | 154.76 | 28.69 | 1940.64 | 126.96 | 17.00 | 1386.18 | | | |
| 20 | 145.65 | 13.21 | 687.55 | 107.81 | 16.57 | 1574.08 | | | |
| 21 | 136.43 | 24.26 | 2357.39 | 96.15 | 12.17 | 828.30 | | | |
| 22 | 121.28 | 7.78 | | | | | | | 617.67 |
| 23 | 101.98 | 17.50 | 1542.78 | | | | | | |
| 24 | | | | | | | | | |

| No. | Mol. Weight | Height | Raw Vol. | Mol. Weight | Height | Raw Vol. | Mol. Weight | Height | Raw Vol. |
|-----|------------|--------|----------|------------|--------|----------|------------|--------|----------|
| 1 | 343.00 | 99.67 | 17050.18 | 314.44 | 28.79 | 2656.47 | 276.88 | 18.48 | 2240.65 |
| 2 | 332.67 | 101.37 | 13589.27 | 304.96 | 25.32 | 2323.24 | 259.19 | 87.87 | 11619.45 |
| 3 | 320.57 | 49.01 | 5604.02 | 258.77 | 27.89 | 4805.85 | 250.57 | 66.70 | 11035.77 |
| 4 | 309.91 | 86.81 | 11798.18 | 248.56 | 87.08 | 14860.81 | 246.17 | 35.34 | 4590.73 |
| 5 | 306.44 | 64.48 | 7092.42 | 241.46 | 42.54 | 6996.39 | 239.91 | 37.68 | 6298.74 |
| 6 | 293.40 | 38.10 | 8906.78 | 226.76 | 29.33 | 4126.01 | 234.56 | 44.50 | 7271.15 |
| 7 | 285.48 | 112.81 | 30135.00 | 220.64 | 33.99 | 8188.92 | 225.31 | 47.52 | 5839.38 |
| 8 | 272.02 | 104.37 | 21337.22 | 211.94 | 64.97 | 8671.23 | 222.43 | 40.63 | 57 |
| 9 | 261.29 | 53.07 | 6784.40 | 186.72 | 82.40 | 15177.27 | 217.47 | 39.91 | 76 |
| 10 | 249.77 | 68.90 | 11679.56 | 183.15 | 67.37 | 10604.46 | 197.02 | 78.59 | 40673.98 |
| 11 | 246.37 | 43.43 | 4293.62 | 172.83 | 67.72 | 19936.67 | 187.12 | 88.17 | 34021.42 |
| 12 | 241.07 | 68.84 | 14703.11 | 163.10 | 51.21 | 7078.85 | 164.15 | 84.42 | 29200.69 |
| 13 | 224.58 | 70.62 | 19025.62 | 160.32 | 54.44 | 11530.01 | 151.29 | 47.29 | 8226.46 |
| 14 | 215.72 | 59.75 | 15853.78 | 153.91 | 137.84 | 15588.69 | 145.12 | 36.93 | 5671.63 |
| 15 | 208.55 | 49.19 | 12777.38 | 126.03 | 43.79 | 13319.07 | 138.87 | 47.00 | 14054.99 |
| 16 | 202.27 | 61.31 | 20719.82 | 116.68 | 43.56 | 7466.26 | 129.13 | 59.28 | 13161.21 |
| 17 | 187.93 | 59.34 | 27199.91 | 98.90 | 23.84 | 8466.17 | 124.10 | 54.58 | 8519.63 |
| 18 | 181.97 | 49.80 | 9960.07 | 86.85 | 38.26 | 9871.00 | 112.64 | 39.63 | 3869.96 |
| 19 | 164.15 | 54.40 | 14547.29 | | | | 104.28 | 33.19 | 5150.07 |
| 20 | 150.00 | 51.09 | 15802.38 | | | | 97.18 | 50.17 | 16328.05 |
| 21 | 145.44 | 47.14 | 11179.48 | | | | 94.64 | 48.26 | 14702.44 |
| 22 | 116.17 | 29.51 | 7583.66 | | | | 84.77 | 23.57 | 6174.90 |
| 23 | 94.43 | 15.26 | 2510.88 | | | | | | |
| 24 | 82.74 | 22.83 | 3251.35 | | | | | | |

Deposits

Applicant has made a deposit of at least 2500 seeds of Sunflower Hybrid PAN 9501 with American Type Culture Collection (ATCC), Manassas, Va. 20110-2209 USA, ATCC Deposit No. 203,526. The seeds were deposited with the ATCC on Dec. 21, 1998. This deposit of Sunflower Hybrid PAN 9501 will be maintained in the ATCC depository, which is a public depository, for a period of 30 years, or for 5 years after the most recent request, or for the enforceable life of the patent, whichever is longer, and will be replaced if it becomes nonviable during that period. Additionally, Applicant has satisfied all the requirements of 37 C.F.R. § § 1.801–1.809, including providing an indication of the viability of the sample. Applicant imposes no restrictions on the availability of the deposited material from the ATCC after the issuance of a patent from this application. However, Applicant has no authority to waive any restrictions imposed by law on the transfer of biological material or its transportation in commerce. Applicant does not waive any infringement of Applicant's rights granted under this patent.

What is claimed is:

1. A hybrid sunflower seed designated PAN 9501, the seeds of which have been deposited as ATCC Accession No. 203526.

2. A hybrid sunflower plant arising from the hybrid sunflower seed of claim 1.

3. A regenerable tissue from the hybrid sunflower seed of claim 1 or the hybrid sunflower plant of claim 2.

4. A sunflower plant regenerated from the regenerable tissue of claim 3 with all the morphological and physiological characteristics of PAN 9501.

5. A callus grown from the regenerable tissue of claim 3, the callus capable of undergoing embryogenesis.

6. A sunflower plant regenerated from the callus of claim 5 with all the morphological and physiological characteristics of PAN 9501.

7. A sunflower seed from the plant of claim 6.

8. The sunflower zygote of claim 10, in which the first gamete is selected from the group consisting of an egg cell and a sperm nucleus.

9. A sunflower seed arising from the zygote of claim 10.

10. A sunflower plant arising from the sunflower seed of claim 12.

11. A process of producing a sunflower seed, comprising the steps of:

provi ding a hybrid sunflower plant designated PAN 9501, representative seed of which have been deposited as ATCC Accession No. 203526, a gamete arising therefrom; and fertilizing the gamete such that the sunflower seed arises from the fertilized gamete.

12. The process of claim 8, in which the gamete comprises an egg cell.

13. A sunflower zygote arising from a fertilization event, the fertilization event a union of a first gamete and a second gamete, the first gamete arising from a hybrid sunflower plant designated as PAN 9501, representative seed of which having been deposited as ATCC Accession No. 203526.

* * * * *

UNITED STATES PATENT AND TRADEMARK OFFICE
CERTIFICATE OF CORRECTION

PATENT NO. : 6,066,787
DATED : May 23, 2000
INVENTOR(S) : Johan J.W. Potgieter

It is certified that error appears in the above-identified patent and that said Letters Patent is hereby corrected as shown below:

Column 7,
Line 58, "branching or" should be -- branching, or --.

Column 8,
Line 42, "stripped" should be -- striped --.
Line 50, "stripping" should be -- striping --.

Column 9,
Line 9, "iii" should be -- ii --.

Column 10,
Line 56, "Based" should be -- * Based --.
Line 58, " * As" shouold be -- ** As --.
Line 59, "  Based" should be -- * Based --.
Line 63, "Values" should be -- + Values --.

Columns 11 and 12,
In Example 3 table should read as follows:

| HYBRID | SEED YIELD[1] | | PCT OIL (10%) | OIL YIELD (LBS/A) | DAYS TO FLOWER |
|---|---|---|---|---|---|
| | LBS/A | Rank | | | |
| LOCATIONS | 8 | | | | |
| PAN 9501 | 2517 | 2 | | | |
| CARGILL 187 | 2035 | 28 | | | |
| CARGILL 270 | -- 1999 -- | . 31 | | | |
| -- DEKALB -- 3790 | 1996 | 32 | | | |
| -- DEKALB -- 3904 | 2074 | 25 | | | |
| -- MEAN -- | 2139 | | | | |
| C.V. (%) | 16 | | | | |
| LSD (0.2) | 103 | | | | |

For the statement under Example 3, there should be a footnote number before the first word -- [1]Analysis -- and "all her traits" should read -- all other traits --.

Column 13,
Line 27, "Days" should be -- *Days --.

UNITED STATES PATENT AND TRADEMARK OFFICE
CERTIFICATE OF CORRECTION

PATENT NO. : 6,066,787
DATED : May 23, 2000
INVENTOR(S) : Johan J.W. Potgieter

It is certified that error appears in the above-identified patent and that said Letters Patent is hereby corrected as shown below:

Column 14,
Line 66, "parafilm" should be -- Parafilm™ --.
Line 67, "+" should be -- ± --.

Columns 15 and 16,
In EXAMPLE 5, the first column in the table should read as follows:

---

HYBRIDS

---

-- 9501
HA30DA
HA89A
P801R
P274R --

Column 18,
Line 51, insert -- an equal -- between "with" and "volume".
Line 52, "enol" should be -- bromophenol --.
Line 53, insert -- 90° C-- between "at" and "and".
Line 56, "de" should be -- acrylamide --.
Line 57, insert -- W) for -- between "55" and "20".
Line 58, "oresis" should be -- electrophoresis --.
Line 59, insert -- dye) was -- between "slower" and "2/3".
Line 60, insert -- visualize -- after "to".

Column 19, and 20,
In AFLP Characterization of PAN 9501 table should read as follows:

There are six column headings which should read:

| -- Primer Pair A -- | -- Primer Pair B -- | -- Primer Pair C -- |
|---|---|---|
| No. Mol. Weight Height Raw Vol. | Mol. Weight Height Raw Vol. | Mol. Weight Height Raw Vol. |

AFLP Characterization of PAN 9501 table: Primer Pair F, No. 8, Raw Vol., "57" should be -- 5778.65 --.
AFLP Characterization of PAN 9501 table: Primer Pair F, No. 9, Raw Vol., "76"

UNITED STATES PATENT AND TRADEMARK OFFICE
CERTIFICATE OF CORRECTION

PATENT NO. : 6,066,787
DATED : May 23, 2000
INVENTOR(S) : Johan J.W. Potgieter

It is certified that error appears in the above-identified patent and that said Letters Patent is hereby corrected as shown below:

AFLP Characterization of PAN 9501 table: Should have a footnote that reads -- Bold indicates molecular markers, 30-330 bp DNA AFLP™ Ladder obtained from GIBCOBRL, supplied by Life Technologies, Inc. --.

Column 20,
Line 65, the claim number "8." should be -- 11. --.

Column 21,
Line 1, the claim number "9." should be -- 12. --.
Line 2, the claim number "10." should be -- 13. --.
Line 4, the claim number "11." should be -- 8. --.

Column 22,
Line 3, the claim number "12." should be -- 9. --.
Line 5, the claim number "13." should be -- 10. --.

Columns 11 and 12,
In the AGRONOMIC DATA table, the first column should read as follows:

| SEED YIELD[1] (LBS/A) | PCT OIL (10%) | OIL YIELD (LBS/A) |
|---|---|---|
| -- LOCATIONS | | |
| PAN 9501 | | |
| CARGILL 187 | | |
| MEAN | | |
| C.V. (%) | | |
| LSD (0.2) | | |
| LOCATIONS | | |
| PAN 9501 | | |
| CARGILL 187 | | |
| MEAN | | |
| C.V. (%) | | |
| LSD (0.2) | | |
| LOCATIONS | | |
| PAN 9501 | | |
| CARGILL 187 | | |
| MEAN | | |
| C.V. (%) | | |
| LSD (0.2) -- | | |

UNITED STATES PATENT AND TRADEMARK OFFICE
CERTIFICATE OF CORRECTION

PATENT NO. : 6,066,787
DATED : May 23, 2000
INVENTOR(S) : Johan J.W. Potgieter

It is certified that error appears in the above-identified patent and that said Letters Patent is hereby corrected as shown below:

For the statement under AGRONOMIC DATA, there should be a footnote number before the first word -- [1]Analysis -- and "all her traits" should read -- all other traits --.

| -- Primer Pair D -- | | | | -- Primer Pair E -- | | | -- Primer Pair F -- | | |
|---|---|---|---|---|---|---|---|---|---|
| No. | Mol. Weight | Height | Raw Vol. | Mol. Weight | Height | Raw Vol. | Mol. Weight | Height | Raw Vol. |

AFLP Characterization of PAN 9501 table: Primer Pair A, No. 5, Mol. Weight, "256.01" should be -- 286.01 --.
AFLP Characterization of PAN 9501 table: Primer Pair B, No. 5, Mol. Weight, "288.08" should be -- 288.06 --.
AFLP Characterization of PAN 9501 table: Primer Pair A, No. 6, Mol. Weight, "272.69" should be -- 272.69 --.
AFLP Characterization of PAN 9501 table: Primer Pair B, No. 15, Mol. Weight, should be highlighted in bold.
AFLP Characterization of PAN 9501 table: Primer Pair C, No. 9, Raw Vol., "647.54" should be -- 847.54 --.
AFLP Characterization of PAN 9501 table: Primer Pair A, No. 22, Raw Vol., please insert -- 617.67 --.
AFLP Characterization of PAN 9501 table: Primer Pair C, No. 22, Raw Vol., please delete "617.67".
AFLP Characterization of PAN 9501 table: Primer Pair D, No. 1, Raw Vol., "17050.18" should be -- 17050.16 --.
AFLP Characterization of PAN 9501 table: Primer Pair D, No. 9, Raw Vol., "6784.40" should be -- 8784.40 --.
AFLP Characterization of PAN 9501 table: Primer Pair D, No. 11, Mol. Weight, "246.37" should be -- 246.57 --.
AFLP Characterization of PAN 9501 table: Primer Pair D, No. 18, Mol. Weight, should be highlighted in bold.
AFLP Characterization of PAN 9501 table: Primer Pair D, Nos. 23-24, Mol. Weight, should be highlighted in bold.

UNITED STATES PATENT AND TRADEMARK OFFICE
CERTIFICATE OF CORRECTION

PATENT NO.   : 6,066,787
DATED        : May 23, 2000
INVENTOR(S)  : Johan J.W. Potgieter It is certified that error appears in the above-identified patent and that said Letters Patent is hereby corrected as shown below:

AFLP Characterization of PAN 9501 table: Primer Pair E, Nos. 1-2, Mol. Weight, should be highlighted in bold.
AFLP Characterization of PAN 9501 table: Primer Pair E, Nos. 12-13, Mol. Weight, should be highlighted in bold.
AFLP Characterization of PAN 9501 table: Primer Pair F, Nos. 1, 4, 6-7, 16, and 18, Mol. Weight, should be highlighted in bold.

Signed and Sealed this

Eleventh Day of December, 2001

*Attest:*

NICHOLAS P. GODICI
*Attesting Officer*  Acting Director of the United States Patent and Trademark Office